US011707491B2

United States Patent
Wang et al.

(10) Patent No.: US 11,707,491 B2
(45) Date of Patent: Jul. 25, 2023

(54) METHODS OF TREATING NEURODEGENERATIVE DISORDERS

(71) Applicant: Board of Supervisors of Louisiana State University and Agricultural and Mechanical College, Baton Rouge, LA (US)

(72) Inventors: Yuping Wang, Shreveport, LA (US); Xiaohong Lu, Shreveport, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 15/811,602

(22) Filed: Nov. 13, 2017

(65) Prior Publication Data
US 2018/0133262 A1 May 17, 2018

Related U.S. Application Data

(60) Provisional application No. 62/420,660, filed on Nov. 11, 2016.

(51) Int. Cl.
| | |
|---|---|
| *A61K 35/50* | (2015.01) |
| *A61K 35/545* | (2015.01) |
| *A61K 35/30* | (2015.01) |
| *A61K 39/00* | (2006.01) |
| *C12N 5/0797* | (2010.01) |
| *C12Q 1/6883* | (2018.01) |
| *C12N 5/0793* | (2010.01) |

(52) U.S. Cl.
CPC .............. *A61K 35/50* (2013.01); *A61K 35/30* (2013.01); *A61K 35/545* (2013.01); *C12N 5/0623* (2013.01); *A61K 39/0007* (2013.01); *C12N 5/0619* (2013.01); *C12N 2501/602* (2013.01); *C12N 2510/02* (2013.01); *C12Q 1/6883* (2013.01)

(58) Field of Classification Search
CPC .. A61K 35/50; A61K 35/545; A61K 39/0007; C12N 5/0623; C12N 5/0619; C12N 2501/602; C12N 2510/02
See application file for complete search history.

(56) References Cited

U.S. PATENT DOCUMENTS

| | | | | |
|---|---|---|---|---|
| 2006/0233766 A1* | 10/2006 | Messina | ................. | A61K 35/30 |
| | | | | 424/93.7 |
| 2012/0129835 A1* | 5/2012 | Brennand | .......... | G01N 33/5058 |
| | | | | 514/211.13 |
| 2016/0279171 A1* | 9/2016 | Gurney | .................. | A61K 35/50 |

OTHER PUBLICATIONS

Yan et al., Neurochem. Res., 38:1022-1033 (2013) (Year: 2013).*
Amariglio et al., PLoS Med., 6(2): e1000029 (2009) (Year: 2009).*
Blurton-Jones, PNAS, 106(32):13594-13599 (2009) (Year: 2009).*
Fricker et al., J. Neurosci., 19(14):5990-6005 (1999) (Year: 1999).*
Gage et al., PNAS, 92:11879-11883 (1995) (Year: 1995).*
Kim et al., J. Neurosci. Res., 87:2183-2200 (2009) (Year: 2009).*
Ladran et al., WIREs Syst. Biol. Med., 5:701-715 (2013) (Year: 2013).*
Park et al., Placenta, 32:269-276 (2011) (Year: 2011).*
Portmann-Lanz et al., Am. J. Obstet. Gynecol., 202:294.e1-11 (2010) (Year: 2010).*
Tincer et al., YJBM 89:23-35 (2016) (Year: 2016).*
Semenov et al., Am. J. Obstet. Gynecol., 202(193):1-13 (2010) (Year: 2010).*
Poloni et al., Cytother., 10(7):690-697 (2008) (Year: 2008).*
Portmann-Lanz et al., Am. J. Obst. Gyn., 194:664-673 (2006) (Year: 2006).*
Igura et al., Cytother., 6(6):543-553 (2004) (Year: 2004).*
Abumaree et al., Stem Cell Rev. Rep., 9:16-31 (2013) (Year: 2013).*
Katsiani et al., Cell Tissue Bank, 17:517-529 (2016) (Year: 2016).*
Mathews et al., Sci. Reports, 5(10054):1-10 (2015) (Year: 2015).*
Parolini et al., Stem Cells, 26:300-311 (2008) (Year: 2008).*
Yang et al., Stem Cell Investig., 1(18):1-9 (2014) (Year: 2014).*
Gonzales-Portillo, Gabriel S., et al. "Stem cell therapy for neonatal hypoxic-ischemic encephalopathy." Frontiers in neurology, 2014, vol. 5, Article 147, p. 1-10.*
Jones et al., PLoS ONE, 2012, vol. 7, Issue 9: e43395, p. 1-15, doi:10.1371/journal.pone.0043395.*

* cited by examiner

*Primary Examiner* — Kade Ariani
(74) *Attorney, Agent, or Firm* — Jones Walker LLP

(57) ABSTRACT

A method of treating a mammal with one of a central nervous system injury and a neurodegenerative disorder comprising isolating, culturing, and generating neural progenitor cells from a mammalian placenta, and transplanting the placenta derived neural progenitor cells into a brain of the mammal.

6 Claims, 4 Drawing Sheets
(4 of 4 Drawing Sheet(s) Filed in Color)

METHODS OF TREATING NEURODEGENERATIVE DISORDERS

CROSS REFERENCE TO RELATED APPLICATIONS/PRIORITY

The present invention claims priority to United States Provisional Patent Application No. 62/420,660, filed Nov. 13, 2016, which is incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

BACKGROUND

Brain injury such as acute asphyxia/hypoxia at the time of birth remains a significant cause of perinatal death of long-term disability. This medical condition affects approximately 4 million neonates and accounts for nearly 25% of neonatal deaths (about 1 million newborns) worldwide annually. Acute asphyxia/hypoxia is one of the major causes of cerebral palsy (CP). Currently, there are only limited medical treatments available for treating birth induced-brain injury. Thus, there is a clear, but seemingly irresolvable need for the development of better therapeutic strategy to treat patients with brain injury and neurodegenerative disorders.

SUMMARY

Wherefore, it is an object of the present invention to overcome the above mentioned shortcomings and drawbacks associated with the current technology. The present invention is directed to methods and materials that satisfy the above shortcomings and drawbacks.

The presently claimed invention also relates to methods of treating a mammal with one of a central nervous system injury and a neurodegenerative disorder comprising isolating, culturing, and generating neural progenitor cells from a mammalian placenta; and transplanting the placenta derived neural progenitor cells into a brain of the mammal. Alternative embodiments include wherein the method treats a central nervous system injury. Alternative embodiments include wherein the central nervous system injury is a brain injury. Alternative embodiments include wherein the brain injury is birth induced-brain injury. Alternative embodiments include wherein the brain injury is acute asphyxia/ hypoxia. Alternative embodiments include wherein the method treats a neurodegenerative disorder. Alternative embodiments include wherein the neurodegenerative disorder is one of Alzheimer's disease, Amyotrophic lateral sclerosis, Friedreich's ataxia, Huntington's disease, Lewy body disease, Parkinson's disease, Spinal muscular atrophy, Alpers' Disease, Batten Disease, Cerebro-Oculo-Facio-Skeletal Syndrome (COFS), Corticobasal Degeneration, Gerstmann-Straussler-Scheinker Disease, Kuru, Leigh's Disease, Monomelic Amyotrophy, Multiple System Atrophy, Multiple System Atrophy with Orthostatic Hypotension (Shy-Drager Syndrome), Neurodegeneration with Brain Iron Accumulation, Opsoclonus Myoclonus, Prion Diseases, Progressive Multifocal Leukoencephalopathy, Striatonigral Degeneration, Transmissible Spongiform Encephalopathies (Prion Diseases), Alexander disease, Alpers-Huttenlocher syndrome, Alpha-methylacyl-CoA racemase deficiency, Andermann syndrome, Arts syndrome, Ataxia neuropathy spectrum, Ataxia with oculomotor apraxia, Autosomal dominant cerebellar ataxia, deafness, and narcolepsy, Autosomal recessive spastic ataxia of Charlevoix-Saguenay, Beta-propeller protein-associated neurodegeneration, cerebral palsy (CP), CLN1 disease, CLN10 disease, CLN2 disease, CLN3 disease, CLN4 disease, CLN6 disease, CLN7 disease, CLN8 disease, Congenital insensitivity to pain with anhidrosis, Familial encephalopathy with neuroserpin inclusion bodies, Fatty acid hydroxylase-associated neurodegeneration, GM2-gangliosidosis, AB variant, Hereditary sensory and autonomic neuropathy type IE, Hereditary sensory and autonomic neuropathy type II, Hereditary sensory and autonomic neuropathy type V, Infantile neuroaxonal dystrophy, Infantile-onset ascending hereditary spastic paralysis, Infantile-onset spinocerebellar ataxia, Juvenile primary lateral sclerosis, Marinesco-Sjögren syndrome, Mitochondrial membrane protein-associated neurodegeneration, Multiple system atrophy, Neuromyelitis optica, Pantothenate kinase-associated neurodegeneration, Polycystic lipomembranous osteodysplasia with sclerosing leukoencephalopathy, Progressive external ophthalmoplegia, Riboflavin transporter deficiency neuronopathy, and Sandhoff disease. Alternative embodiments include wherein the mammal is a human. Alternative embodiments include wherein the mammalian placenta is a human placenta. Alternative embodiments include wherein the mammalian placenta is a term placenta. Alternative embodiments include wherein the neural progenitor cells are nestin+ neural progenitor cells. Alternative embodiments include wherein the neural progenitor cells are SOX2+ neural progenitor cells. Alternative embodiments include wherein the neural progenitor cells are vimentin+ neural progenitor cells. Alternative embodiments include wherein the neural progenitor cells are nestin+, SOX2+, and vimentin+ neural progenitor cells.

The presently claimed invention further relates to a method of obtaining a neural progenitor cell comprising isolating, culturing, and generating the neural progenitor cells from a mammalian placenta. Alternative embodiments include wherein the neural progenitor cells are nestin+ neural progenitor cells. Alternative embodiments include wherein the neural progenitor cells are SOX2+ neural progenitor cells. Alternative embodiments include wherein the neural progenitor cells are vimentin+ neural progenitor cells. Alternative embodiments include wherein the neural progenitor cells are nestin+, SOX2+, and vimentin+ neural progenitor cells. Alternative embodiments include wherein the mammalian placenta is a term human placenta.

The presently claimed invention further relates to a human neural progenitor cell produced by isolating, culturing, and generating the neural progenitor cells from a mammalian placenta.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which:

FIG. 4A is an image of placenta derived NPCs after transfected with AAV-GFP in culture. GFP positive cells indicate efficacy of AAV-GFP transfection. FIG. 4B is an image of a mouse brain 4 weeks after transplantation of placenta-derived NPCs that are transfected with AAV-GFP. The area of FIG. 4B indicated by the symbol "I" is a densely packed graft core at the injection site. The area of FIG. 4B indicated by the symbols "II" and "III" are GFP-positive transplanted cells migrated from the injection site. GFP is used as an indicator of transplanted cells, transplanted placental cells (green) and astrocytes (red). FIG. 4C shows 3D confocal Z stacks of a GFP-positive differentiated neural cell. The cell exhibits typical differentiated neural cell phenotype with cell body (soma), dendrites, and axon. The magnified portions (I and II) show differentiated dendrites and dendritic spines and growing axons with axon boutons.

DETAILED DESCRIPTION

Figure 1:
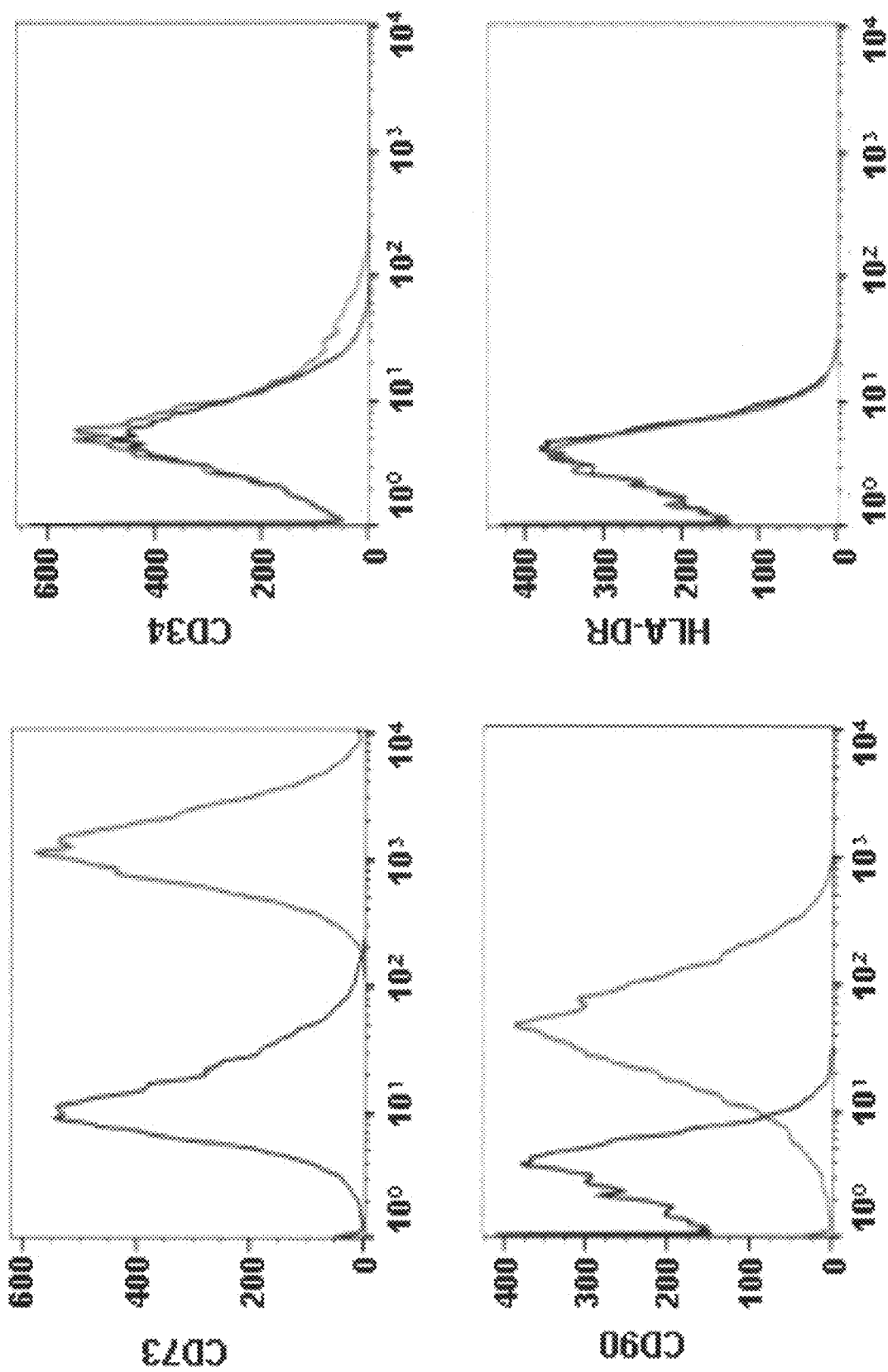
FIG. 1 is four line graphs showing positive expression of CD73 and CD90, but not CD34 and HLA-DR, detected by flow cytometry in cells derived from human placenta, where the black line is unstained control and the red line is stained cells. CD73 and CD90 are mesenchymal stem cell markers and these cells negatively express CD 34 (an endothelial cell marker) and HLA-DR (human leukocyte antigen-antigen D related).

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIG. 1, a brief description concerning the various components of the present invention will now be briefly discussed. The invention relates to the present process relates individually and collectively to 1) generation of nestin+/SOX2+/vimentin+ mesenchymal stem cells/neural progenitor cells (NPCs) from the human term placenta and 2) transplantation of placenta-derived nestin+/SOX2+/vimentin+ NPCs into a mammal's brain for therapeutic effect, including treatment of a disease, pre-disease state, genetic defect, and/or neurodegenerative disorders. Transplanted human placenta derived NPCs are able to differentiate into neuronal lineage cells in vivo. Human placenta-NPCs are able to differentiate into neuronal lineage cells in vivo. Human placenta-NPCs are isolated by enzymatic digestion of placental villous tissue using trypsein and DNAse. No mesenchymal stem cells/neural progenitor cells are eliminated by Percoll gradient centrifugation, magnetic bead separation, and/or cultured with Dulbecco's Modified Eagle Medium (DMEM) supplemented with fetal bovine serum and antibiotic-antimycotic solution. Cells are characterized by positive expression of stem cell/progenitor cell markers CD133 and Oct-4; mesenchymal stem cell markers CD73 and CD90; and neural stem/progenitor cell markers nestin, SOX2, and vimentin. In vivo differentiation of placenta-derived NPCs into neuronal lineage cells after transplantation into the brain is demonstrated by identification of GFP-positive neurons in the brain tissue in the study animals.

These data indicate that undifferentiated placenta-derived NPCs are able to self-differentiate into neuronal lineage cells in vivo after engrafted into the brain.

Human placenta represents the richest source of mesenchymal stem cells (MSCs) in human tissues. MSCs have an extremely high differentiation potential with widespread applications in the restoration of cardiovascular and central nervous system injury. MSCs from placental tissue are pluripotent and have shown to be able to differentiate into multiple lineage cell types, including osteoblasts, chondrocytes, myocytes, adipocytes, and even endothelial cells. Compared to bone marrow stem cells or inducible pluripotent stem cells (iPSC) from adult cell/tissue, which may be ethically controversial, of limited quantity, finite, and genetically unsuitable, placental tissue is considered medical waste after birth; they possess pluripotency; they are available in nearly unlimited supply; and they have low immunogenicity. Recently, neural cell identity reprogramming strategies in which stem cells regenerate neural architecture and functional circuits in vivo have been emerged with therapeutic potential to treat CNS injury, including brain injury, and neurodegenerative disorders. Therefore, the inventors' findings of neuronal progenitor cell characterization of placental MSCs/NPCs and their in vivo self-differentiation potential into neuronal cells make the nestin+/SOX2+ positive placenta-derived NPCs an ideal source of stem/progenitor cells in regeneration medicine in treating brain injury, including acute asphyxia/hypoxia, and treating neurodegenerative disorders, including, for example, Alzheimer's disease, Amyotrophic lateral sclerosis, Friedreich's ataxia, Huntington's disease, Lewy body disease, Parkinson's disease, Spinal muscular atrophy, Alpers' Disease, Batten Disease, Cerebro-Oculo-Facio-Skeletal Syndrome (COFS), Corticobasal Degeneration, Gerstmann-Straussler-Scheinker Disease, Kuru, Leigh's Disease, Monomelic Amyotrophy, Multiple System Atrophy, Multiple System Atrophy with Orthostatic Hypotension (Shy-Drager Syndrome), Neurodegeneration with Brain Iron Accumulation, Opsoclonus Myoclonus, Prion Diseases, Progressive Multifocal Leukoencephalopathy, Striatonigral Degeneration, Transmissible Spongiform Encephalopathies (Prion Diseases), Alexander disease, Alpers-Huttenlocher syndrome, Alpha-methylacyl-CoA racemase deficiency, Andermann syndrome, Arts syndrome, Ataxia neuropathy spectrum, Ataxia with oculomotor apraxia, Autosomal dominant cerebellar ataxia, deafness, and narcolepsy, Autosomal recessive spastic ataxia of Charlevoix-Saguenay, Beta-propeller protein-associated neurodegeneration, cerebral palsy (CP), CLN1 disease, CLN10 disease, CLN2 disease, CLN3 disease, CLN4 disease, CLN6 disease, CLN7 disease, CLN8 disease, Congenital insensitivity to pain with anhidrosis, Familial encephalopathy with neuroserpin inclusion bodies, Fatty acid hydroxylase-associated neurodegeneration, GM2-gangliosidosis, AB variant, Hereditary sensory and autonomic neuropathy type IE, Hereditary sensory and autonomic neuropathy type II, Hereditary sensory and autonomic neuropathy type V, Infantile neuroaxonal dystrophy, Infantile-onset ascending hereditary spastic paralysis, Infantile-onset spinocerebellar ataxia, Juvenile primary lateral sclerosis, Marinesco-Sjögren syndrome, Mitochondrial membrane protein-associated neurodegeneration, Multiple system atrophy, Neuromyelitis optica, Pantothenate kinase-associated neurodegeneration, Polycystic lipomembranous osteodysplasia with sclerosing leukoencephalopathy, Progressive external ophthalmoplegia, Riboflavin transporter deficiency neuronopathy, and Sandhoff disease. Neurodegenerative disorders include both disease and pre-disease states.

The inventors have established the isolation, culture, and generation of nestin+/SOX2+/vimentin+ neural progenitor cells from the human term placenta. The inventors have further demonstrated that human placenta-derived NPCs can self-differentiate into neurons and neuronal lineage cells after transplanted into the brain. These cells survived in the mouse brain and functionally integrated with the existing neuronal circuitry. These findings provide a new insight that placenta-derived NPCs may self-differentiate into neurons and neuronal lineage cells after being transplanted into the brain. These cells survived in the mouse brain and functionally integrated with the existing neuronal circuitry. These findings provide a new insight that placenta-derived MSCs/NPCs are a promising candidate source of stem/neural progenitor cell therapy and have a significant impact in the field of personalized medicine to treat central nervous system injury and neurodegenerative diseases/disorders.

Turning to FIG. 1, placental cells are shown to express CD73 and CD90, markers of mesenchymal stem cells. Flow-cytometry detection of CD73, CD90, CD34, and HAS-DR in cells isolated from human placenta are shown. CD73 and CD90 are markers of mesenchymal stem cells, CD34 is a marker of endothelial progenitor cells. HLA-DR is an MHC class II cell surface receptor and it is negatively expressed in mesenchymal stem cells.

Figure 2:
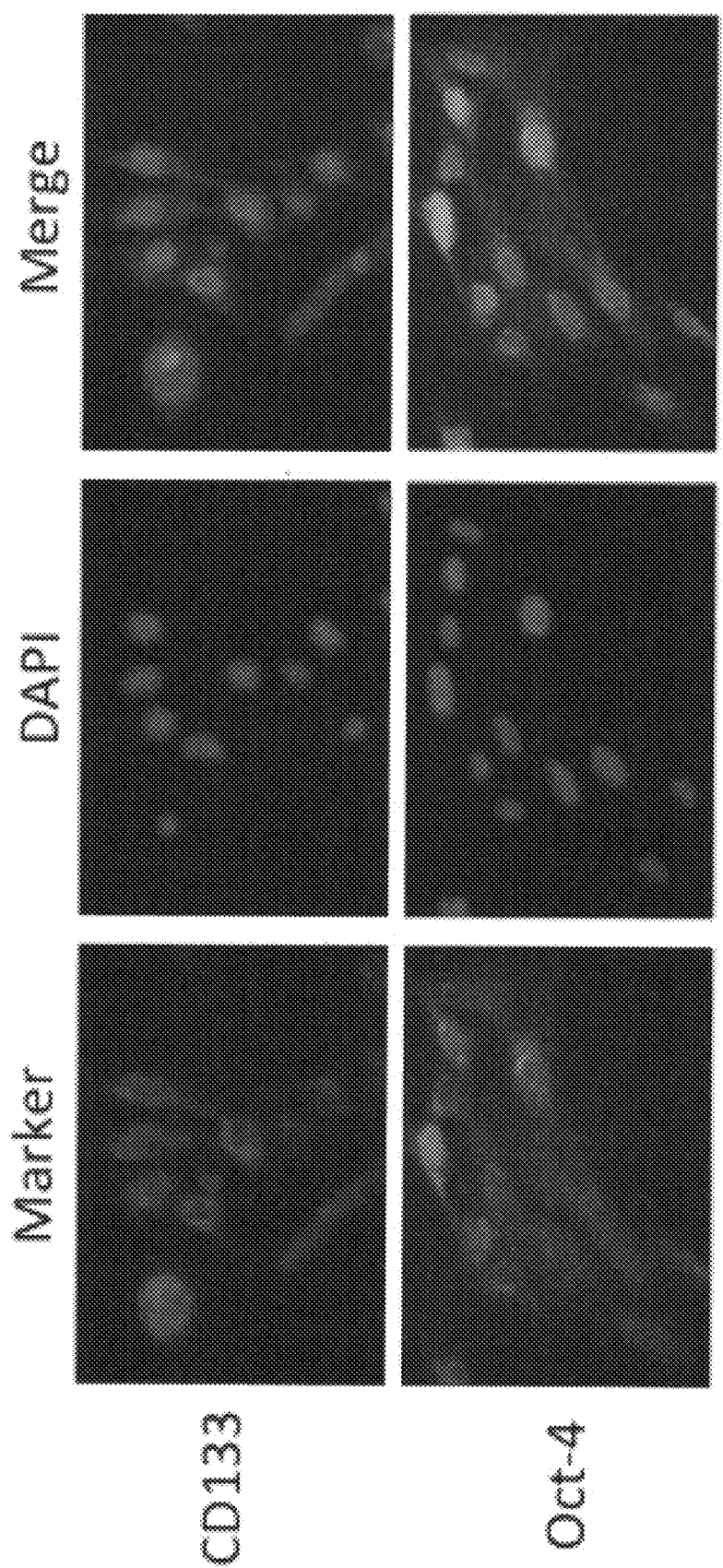
FIG. 2 is six micrographs showing positive expression of CD133 and Oct-4 detected by fluorescent staining in cells from human placenta. CD133 and Oct-4 are stem cell/progenitor cell markers.

Turning to FIG. 2, placenta cells are shown to express CD133 and Oct-4, markers of stem/progenitor cells. Expression of CD133 and Oct-4 by placental cells detected by fluorescent staining. CD133 and Oct-4 are stem cell/progenitor cell markers.

Figure 3:
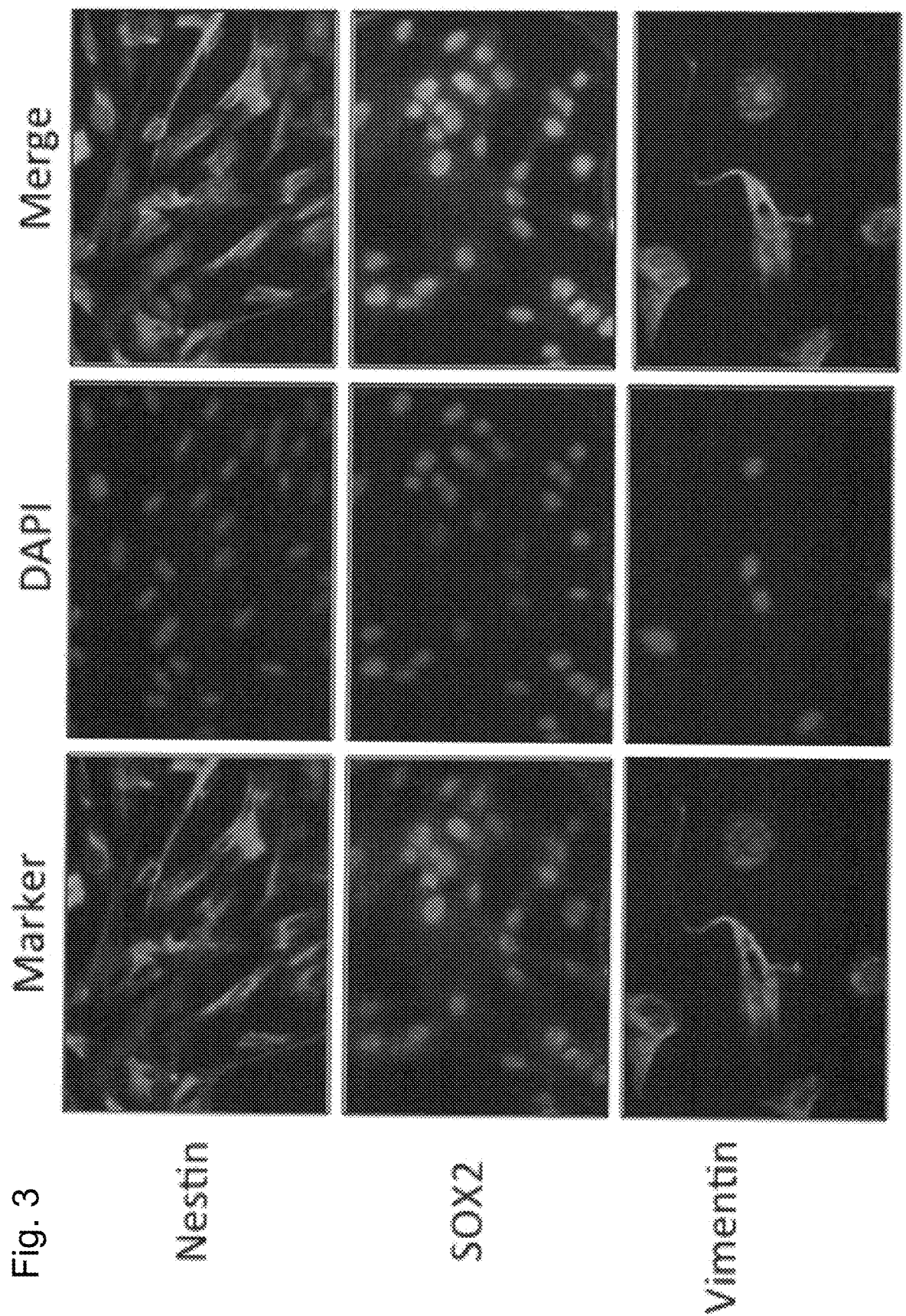
FIG. 3 is nine micrographs showing positive expression of nestin, SOX2, and vimentin detected by fluorescent staining in cells derived from human placenta. Nestin, SOX2, and vimentin are neural progenitor cell markers. SOX2 and vimentin are also considered glial-astrocyte markers.

Turning to FIG. 3, placenta cells are shown to express nestin, SOX2, and vimentin, markers of neural stem/progenitor cells. Expression of nestin, SOX2, and vimentin by placental cells are detected by fluorescent staining. Nestin, SOX2, and vimentin are neural stem cell/progenitor cell markers. SOX2 and vimentin are also considered glial-astrocyte markers.

Figure 4C:
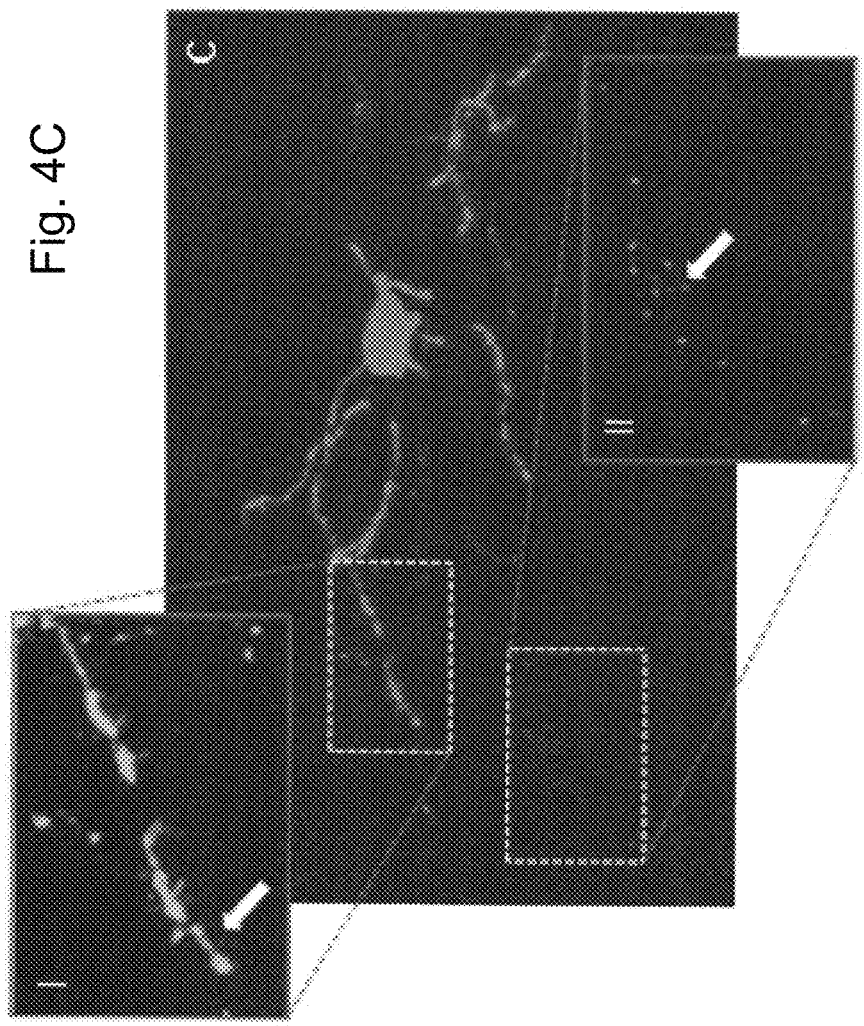
FIGS. 4A-4C show images of human placenta-derived NPCs transfected with AAV-GFP in culture and GFP positive cells 4 weeks after transplantation into the mouse brain.
Figure 4A:
Figure 4B:
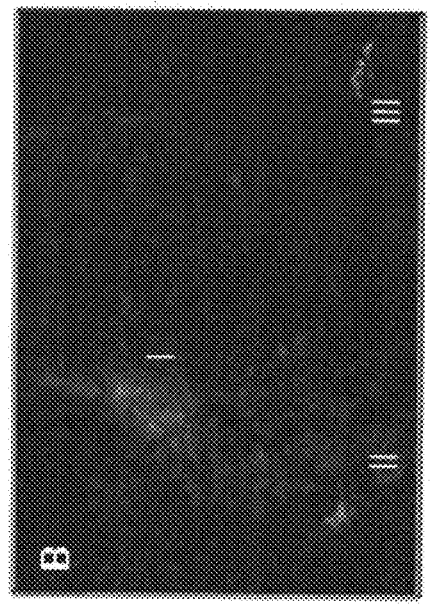

Turning to FIG. 4, differentiation potential of placental cells after implantation into a mouse brain is shown. Images shown are of placental cells transfected with AAV-GFP in culture and GFP positive cells 4 weeks after implantation into the mouse brain. Image A is of placenta cells after transfected with AAV6-GFP in culture. Image B is of a mouse brain 4 weeks after implantation of AAV-GFP infected cells. Image C is 3D confocal Z stacks of a GFP-positive differentiated neural cell. The cell exhibits typical differentiated neural cell phenotype with cell body, dendrites, and axon. The inserts (I and II) show differentiated dendrites and dendritic spines and growing axons with axon boutons.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

Wherefore, We claim:

1. A method of treating a mammal with a central nervous system injury comprising:
   isolating, culturing, and generating neural progenitor cells from placental villous tissue of a term mammalian placenta, the neural progenitor cells being at least one of the neural progenitor cells comprising nestin+, SOX2+, and vimentin+; and
   transplanting the placenta derived neural progenitor cells into a brain of the mammal;
   wherein the central nervous system injury is a birth induced-brain injury and is acute asphyxia/hypoxia; and
   wherein the neural progenitor cells positively express CD133, Oct-4, CD73 and CD90, but do not positively express CD34 and HLA-DR.

2. The method of claim 1 wherein the mammal is a human.

3. The method of claim 1 wherein the mammalian placenta is a human placenta.

4. The method of claim 1 wherein the neural progenitor cells are nestin+, SOX2+, and vimentin+.

5. The method of claim 1 further comprising the step of enzymatically digesting the placental villous tissue.

6. The method of claim 1 further comprising the step of enzymatically digesting the placental villous tissue using trypsin and DNAse.

* * * * *